United States Patent [19]

Slovák et al.

[11] 4,353,368
[45] Oct. 12, 1982

[54] DEVICE FOR HEMODIALYSIS

[75] Inventors: Petr Slovák; Hana Bečvářová; Milan Ruml; Jiří Kracík, all of Prague, Czechoslovakia

[73] Assignee: Ceske vysoke uceni technicke, Prague, Czechoslovakia

[21] Appl. No.: 179,467

[22] Filed: Aug. 19, 1980

Related U.S. Application Data

[63] Continuation-in-part of Ser. No. 973,026, Dec. 26, 1978, abandoned.

[30] Foreign Application Priority Data

Dec. 23, 1977 [CS] Czechoslovakia ............... 8781-77

[51] Int. Cl.³ ............................................. A61M 5/00
[52] U.S. Cl. ................................. 128/214 R; 210/646
[58] Field of Search ........... 128/214 R, 213 A, 213 R; 210/22 R, 22 A

[56] References Cited

U.S. PATENT DOCUMENTS

| 3,946,731 | 3/1976 | Lichtenstein | 128/214 R |
| 3,964,479 | 6/1976 | Boag et al. | 128/214 R |
| 3,965,008 | 6/1976 | Dawson | 210/243 |
| 4,081,372 | 3/1978 | Atkin et al. | 128/214 R |

OTHER PUBLICATIONS

"A Home Peritoneal Dialysate Delivery System", Tenckhoff et al., Trans. Amer. Soc. Artif. Int. Organs, 1969, vol. XV, p. 103.

Primary Examiner—Richard J. Apley
Assistant Examiner—T. J. Wallen

[57] ABSTRACT

A device for hemodialysis provided with: an artery needle, a set of hoses with a bubble trap, a blood pump, a hemodialyzer, a venous needle, a container of a dialyzing solution, a conduit for the dialyzing solution, a unit of sensors for measuring the temperature, conductivity, and pressure of the dialyzing solution, a pump for the dialyzing solution, a hemoglobin detector, an electronic unit and an alarm unit providing audible and visual warning signals. The dialyzing solution is heated to a suitable temperature by a heat exchanger which is supplied with waste heat from the cooling system of an automobile engine. The device may be used in a home and for weekend dialysis, as well as for emergency mobile use.

5 Claims, 1 Drawing Figure

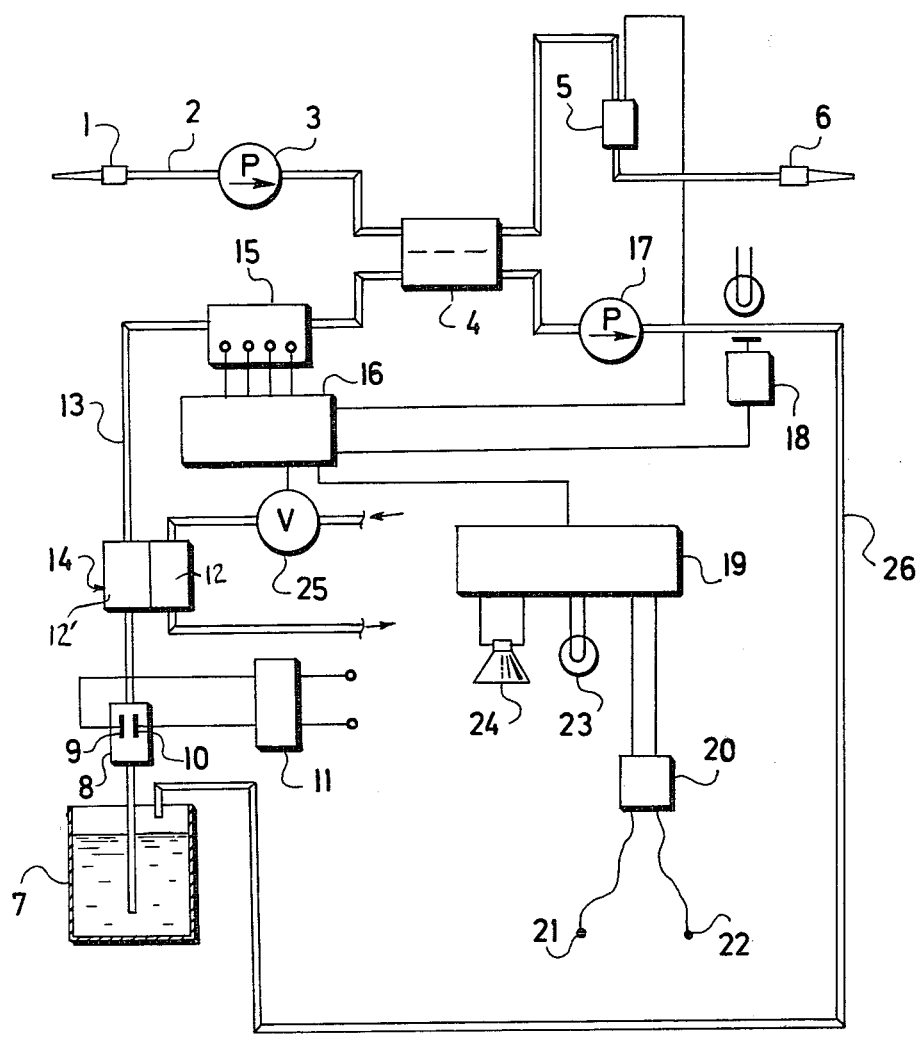

DEVICE FOR HEMODIALYSIS

This application is a continuation-in-part of application Ser. No. 973,026, filed Dec. 26, 1978 now abandoned.

The invention relates to a device for hemodialysis provided with: an artery needle, a set of hoses with a bubble trap, a blood pump, a hemodialyzer, a venous needle, a container of dialyzing solution, a conduit for a dialyzing solution, a unit of sensors of temperature, conductivity and pressure of the dialyzing solution, a pump for the dialyzing solution, a hemoglobin detector, an electronic unit, and an alarm unit providing audible and visual indications.

BACKGROUND OF THE INVENTION

Hitherto known stationary devices for hemodialysis installed in hospitals are usually supplied with electrical energy from the utility power outlets and depend upon the delivery of pressurized water. A dialyzing solution is prepared by means of built-in mixers.

Mobile devices for hemodialysis comprise a container of a dialysis solution, a supply of electrical energy from automobile alternator or generator, and a minimum of those parts that must be sterilized. That is why hoses for dialyzing solution are used only once.

A drawback of known mobile devices for hemodialysis having a container of a dialyzing solution is the rapid increase in the concentration of microorganisms in the unsterile dialyzing solution. If bacterium contamination in the dialyzing solution exceeds a concentration of 1000 microorganisms/ml, then there exists for a patient a risk of pyrogenic and septic complications. A preparation of a dialyzing solution of a low concentration of microorganisms under 100/ml, e.g. from freshly distilled water or from water irradiated by a germicide discharge tube, requires considerable electric power and that is why it is not possible to do it in an ambulance or other automobile. Therefore the dialyzing solution is prepared only from water examined in advance as to bacterium content. Such an examination takes much time.

To heat the dialyzing solution by electric current requires much power from the automobile electric generator. The clinical complications of medical treatment—like decreased blood pressure, vertigo or spasms—can be removed by application of the corresponding medicaments that often decrease the treating effect of hemodialysis. When a device for hemodialysis is used in a self-care operation by a patient who is sleeping or hard of hearing, there is a risk that the patient will not observe the acoustic or optical alarm, and will not correct the operation of the device.

SUMMARY OF THE INVENTION

Some of the mentioned drawbacks may be obviated by the device for hemodialysis according to the invention. Such device comprises an artery needle, a set of hoses with bubble trap, a bloood pump, a hemodialyzer, a venous needle, a container of a dialysis solution, a conduit for the dialyzing solution, a unit of sensors for temperature, conductivity and pressure of the dialyzing solution, a pump for the dialyzing solution, a hemoglobin detector, an electronic unit, and an alarm unit providing audible and visual indications.

The principle of the hemodialyzing device according to the invention resides in the fact, that in the conduit for the dialyzing solution or in the container of the dialyzing solution there is situated a unit for inhibiting the growth of microorganisms in the dialyzing solution. The unit consists of two electrodes connected to an A.C. power source providing a time variable frequency and amplitude output. In the conduit for the dialyzing solution there may be situated a liquid-liquid heat exchanger connected to a source of waste heat from an automobile engine, for example, the heat source may be the radiator of the water cooled engine of an automobile, or a finned heating coil or the like disposed in the path of the discharge of cooling air from such radiator, or in the path of cooling air from air cooled engine of an automobile. The heat exchanger may also be disposed in the container for the dialyzing solution. A source of electric impulses with electrodes connected to the body of a patient may be connected to the output of the alarm unit.

In the container of the dialyzing solution there is situated a unit inhibiting the growth of microorganisms in the dialyzing solution consisting of at least two electrodes connected to an A.C. power source providing a time variable frequency and amplitude output. In the conduit of the dialyzing solution or in the container of the dialyzing solution there is situated a heat exchanger supplied with a waste heat from an automobile engine, and to the output of the alarm unit there is connected a source of electric impulses with electrodes connected to a patient's body.

A unit for treating the dialyzing solution inhibits the growth of microorganisms in the dialyzing solution, and in this way reduces the risk of infection and pyrogenic and septic complications of a medical treatment. It is advantageous also for stationary hemodialyzing devices that recirculate the dialyzing solution, and for devices that regenerate the solution.

The heating of a dialyzing solution by means of a heat exchanger supplied with waste heat from an automobile radiator considerably reduces electrical power consumption from the automobile alternator or generator. It is recommended that the heat exchanger be constructed with a double wall between compartments thereof for the sake of safety. The source of electric impulses with electrodes put onto the patient's body increases the safety during a self-care operation with the hemodialysis device. In case of clinical complications, the source of electrical stimulating impulses by means of electrodes stimulates predetermined definite places of the patient's body. If a sleeping or deaf patient ignores an optical or acoustic alarm, he is awakened by electric impulses. The safety of operation may be increased in this way in a clinical use of a hemodialyzing device in a self-care arrangement.

The invention will now be described by means of the appended drawing in which a schematic arrangement of a mobile device for hemodialysis is shown.

BRIEF DESCRIPTION OF THE DRAWING

The single FIGURE of the drawing is a schematic diagram of a preferred embodiment of the invention.

DETAILED DESCRIPTION OF THE PREFERRED EMBODIMENT

Blood is conducted from the patient's body through an artery needle 1, a set of hoses 2, a blood pump 3, and into a hemodialyzer 4 of ordinary construction. Blood is conducted from the hemodialyzer 4 into a bubble trap 5, the bubble trap containing means for measuring blood pressure which is connected to a pressure sensor of an electronic unit 16. Blood flows back from the bubble trap 5 into the patient's body through a venous needle 6.

A dialyzing solution in a container 7 is conducted through a unit 8 for inhibiting the growth of microorganisms in the solution delivered from container 7. The unit 8 for inhibiting the growth of microorganisms consists of at least two electrodes 9 and 10, which are connected to an A.C. power source 11 providing an electrical output which is time variable in frequency and amplitude. The dialyzing solution passes from unit 8 into a first chamber 12' of a double isolated heat exchanger 14, a second chamber 12 of which is supplied with waste heat from an automobile engine cooling system.

Such cooling system in the embodiment shown is that of a water cooled engine having a radiator (not shown). The heat intake from the top of the radiator is controlled by means of a valve 25 operated by a thermostat in the electronic unit 16. After flowing through said second chamber 12 of the heat exchanger 14, the water returns to the bottom of the radiator. It is advantageous to locate the unit 8 for inhibiting the growth of microorganisms in the dialyzing solution, as well as the heat exchanger 14, in the container 7 of the dialyzing solution. A conduit 13 for the dialyzing solution is connected to a unit 15 of sensors. Outputs of the temperature, conductivity and pressure sensors are connected to the electronic unit 16. The passage of the dialyzing solution through the hemodialyzer 4 is insured with a dialyzing solution pump 17. On the drain part of the conduit 13 for the dialyzing solution there is disposed a hemoglobin detector 18 having its electrical output connected to the electronic unit 16. After passing through the detector 18, the dialyzing solution is returned to the container 7 through pipe 26.

To the output of the electronic unit 16 there is connected an alarm unit 19 with an acoustic alarm 24 and an optical alarm 23 which are switched on if safe operating ranges of the pressure, temperature and conductivity sensors are exceeded. To the output of the alarm unit 19 there is connected a source 20 of electric impuses with electrodes 21 and 22 connected to the patient's body. In the case of clinical complications, the source 20 of the electrical stimulating impulses stimulates predetermined definite places of the patient's body by means of the electrodes 21 and 22. This source 20 is triggered by hand. Electrical impulses awaken the patient if he does not sense the optical or acoustic signals. It is advantageous to arrange the alarm unit 19 so that the source 20 of electrical stimulating impulses may be delayed with respect to the acoustic and optical alarms.

It is to be understood that rigorous precautions are to be observed in the manufacture and testing of the dialyzing system to prevent any possibility of contamination of the dialyzing solution by the liquid coolant of the automobile engine. Thus both chambers of the double isolated heat exchanger 14, the chamber through which engine coolant flows, and the chamber through which dialyzing solution flows, must be tested under pressures, as by compressed air, far exceeding the pressure to which they are subjected during operation of the dialyzing system, to insure that such chambers are and will remain fluid tight and isolated from each other.

The same precautions are to be observed when the source of heat for heating the dialyzing solution is the discharged cooling air of an air cooled automobile engine. In such latter case, the means taking the place of heat exchanger 14 is a device, preferably externally finned, having a single chamber through which the dialyzing solution flows, such device being placed in the discharge path of the engine cooling air. Such device must also be rigorously tested for fluid tightness. The degree of absorption of heat from the engine cooling air by such single chambered dialyzing solution heating means is controlled by thermostatically controlled shutters interposed in the cooling air path upstream of such dialysis solution heating means.

In the preferred embodiment of the device for hemodialysis the unit for hihibiting the growth of microorganisms has rustless electrodes 9 and 10 supplied by current source 11 with a current density of $25 A/m^2$ and a frequency range of between 0.1 Hz and 800 Hz. The source 20 of electrical impules has an output variable between 0.001 W and 1.0 W. The unit 15 of sensors is removable from the device, so that it can be immersed in a sterilizing bath during sterilization. The conduit 13 of the dialyzing solution is designed for one use only, thereafter being thrown away.

The device for hemodialysis of the invention may be used in the home, and for weekend dialysis, as well as for emergency mobile use. Thus although the invention has been illustrated with reference to one preferred embodiment, it is to be expressly understood that the invention may be carried out in other embodiments within the scope of the appended claims.

We claim:
1. A device for hemodialysis comprising a first, arterial blood conducting circuit means comprising an arterial needle adapted to be inserted into an artery of a patient, a first, blood pump means for forwarding blood from the arterial needle, a hemodialyzer having a first chamber receiving arterial blood from the blood pump, a bubble trap receiving arterial blood from the first chamber of the hemodialyzer, and a venous needle receiving arterial blood from the bubble trap, a second, dialyzing solution conducting circuit means comprising a container holding a dialyzing solution, a solution conducting unit containing sensors, a second chamber of the hemodialyzer, a second dialyzing solution pump means for moving the dialyzing solution from the dialyzing solution container through the unit containing sensors into the second chamber of the hemodialyzer, a hemoglobin detector connected to an outlet of said second pump means, an electronic unit provided with acoustic and optical alarms indicating malfunctions of the hemodialysis device, said electronic unit comprising at least two electrodes in the dialyzing solution, and an A.C. power source means connected to said electrodes for providing a sufficient electrical output to said electrodes which is variable in both frequency and amplitude to inhibit the growth of bacteria in the dialyzing solution.

2. A device for hemodialysis as claimed in claim 1, further comprising heat exchanger means having a first chamber connected to said dialyzing solution container and a second chamber adapted to be connected to a source of waste heat from an automobile engine for heating said dialyzing solution.

3. A device for hemodialysis as claimed in claim 2, further comprising a source of electrical pulses triggered into operation by hand and electrodes connected to a patient's body.

4. A device for hemodialysis as claimed in claim 1, further comprising a source of electrical stimulating pulses, and at least two electrodes adapted to be connected to a patient's body.

5. A device for hemodialysis as claimed in claim 3, wherein said source of electrical stimulating pulses is triggered into operation by said optical and acoustic alarms.

* * * * *